United States Patent
Morikawa et al.

(10) Patent No.: US 8,239,015 B2
(45) Date of Patent: Aug. 7, 2012

(54) DISTRACTION DETECTION APPARATUS, DISTRACTION DETECTION METHOD, AND COMPUTER PROGRAM

(75) Inventors: Koji Morikawa, Kyoto (JP); Toru Nakada, Kyoto (JP); Yoshihisa Terada, Osaka (JP)

(73) Assignee: Panasonic Corporation, Osaka (JP)

( * ) Notice: Subject to any disclaimer, the term of this patent is extended or adjusted under 35 U.S.C. 154(b) by 300 days.

(21) Appl. No.: 12/793,263

(22) Filed: Jun. 3, 2010

(65) Prior Publication Data

US 2010/0241021 A1     Sep. 23, 2010

Related U.S. Application Data

(63) Continuation of application No. PCT/JP2009/004771, filed on Sep. 18, 2009.

(30) Foreign Application Priority Data

Sep. 19, 2008    (JP) ................................. 2008-240470

(51) Int. Cl.
*A61B 5/04*      (2006.01)

(52) U.S. Cl. ...................................................... 600/545

(58) Field of Classification Search ................... 600/544, 600/545
See application file for complete search history.

(56) References Cited

U.S. PATENT DOCUMENTS 6,625,485 B2 *   9/2003   Levendowski et al. ....... 600/544
7,574,254 B2 *   8/2009   Milgramm et al. ........... 600/544

FOREIGN PATENT DOCUMENTS

| | | |
|---|---|---|
| JP | 07-329657 | 12/1995 |
| JP | 2004-178367 | 6/2004 |
| JP | 2005-228003 | 8/2005 |
| JP | 2007-000280 | 1/2007 |
| JP | 2007-265377 | 10/2007 |

OTHER PUBLICATIONS

International Search Report for corresponding International Application No. PCT/JP2009/004771 mailed Nov. 24, 2009.

(Continued)

*Primary Examiner* — Navin Natnithithadha
*Assistant Examiner* — Etsub Berhanu
(74) *Attorney, Agent, or Firm* — Renner, Otto, Boisselle & Sklar, LLP

(57) ABSTRACT

The distraction detection apparatus includes: an electroencephalogram detection section for detecting an electroencephalogram signal of a driver; an arousal level estimation section for retaining a first rule of mapping parameter values of an electroencephalogram signal to arousal levels, and estimating an arousal level based on the detected electroencephalogram signal and the first rule; an attention allocation estimation section for retaining a second rule of mapping parameter values of an electroencephalogram signal to attention allocations, and estimating an attention allocation based on the detected electroencephalogram signal and the second rule; a driver state estimation section for retaining a third rule of deriving an amount of attention from an arousal level and an attention allocation, estimating an amount of attention of the driver paid to driving based on the estimated arousal level and attention allocation and the third rule, and classifying a state of the driver into a normal state, a state of reduced attention, or a state of reduced arousal level; and an output section for performing an intervention for the driver based on a result of classification by the driver state classification section.

10 Claims, 15 Drawing Sheets

OTHER PUBLICATIONS

Noriyoshi Matsuo, "Jidosha Unten ni Okeru No Kino Hyoka to No Kassei Shuho", Japanese Journal of Clinical Neurophysiology, vol. 35, No. 5, Yugen Sekinin Chukan Hojin Nippon Rinsho Shinkei Seiri Gakkai, Oct. 1, 2007, p. 329.

Hiroshi Nittono, "Measuring attention to video clips: An application of the probe stimulus technique using event-related brain potentials", Japanese Journal of Physiological Psychology and Psychophysiology, 2006, 24(1), 5-18 (cited in [0046], p. 15 of the specification).

* cited by examiner

| RESULT OF ELECTROENCEPHALOGRAM MEASUREMENT | DETERMINATION |
|---|---|
| AMPLITUDE FOR TASK OTHER THAN DRIVING TASK IS SMALL | ATTENTION IS PAID TO DRIVING (SAFE STATE) |
| AMPLITUDE FOR TASK OTHER THAN DRIVING TASK IS LARGE | ATTENTION IS NOT PAID TO DRIVING (STATE OF DISTRACTION) |

(b)

| RESULT OF ELECTROENCEPHALOGRAM MEASUREMENT | AROUSAL LEVEL | DETERMINATION | |
|---|---|---|---|
| AMPLITUDE FOR TASK OTHER THAN DRIVING TASK IS SMALL | HIGH | ATTENTION IS PAID TO DRIVING | |
| | NORMAL | | |
| | LOW | DRIVING ATTENTION IS ALSO LOW (NOT SAFE) | 11 |
| AMPLITUDE FOR TASK OTHER THAN DRIVING TASK IS LARGE | HIGH | (SOME ATTENTION MAY BE PAID TO DRIVING (MAYBE SAFE) | 12 |
| | NORMAL | DISTRACTED | |
| | LOW | DRIVING ATTENTION IS ALSO LOW (DOZING OFF?) | |

*FIG.2*

| | HARD | NORMAL | EASY |
|---|---|---|---|
| DRIVING TASK | FOLLOW PRECEDING CAR AT 120 Km/h | FOLLOW PRECEDING CAR AT 80 Km/h | NO DRIVING (PASSENGER SEAT CONDITION) |
| DISPLAY-VIEWING TASK | PRESENTATION TIME: 0.4 SECONDS PRESENTATION INTERVAL: 0.2 SECONDS | PRESENTATION TIME: 0.8 SECONDS PRESENTATION INTERVAL: 1.0 SECONDS | NO RESPONSE (IGNORING CONDITION) |

CORRELATION BETWEEN OVERALL
AMOUNT OF ATTENTION AND α WAVES [AVERAGE OF ALL]

CORRELATION COEFFICIENT = 0.78

CORRELATION BETWEEN AMOUNT OF ATTENTION TO SUBTASK
AND P3 AMPLITUDE FOR SUBTASK RESPONSE [AVERAGE OF ALL]

CORRELATION COEFFICIENT = -0.77

*FIG.5*
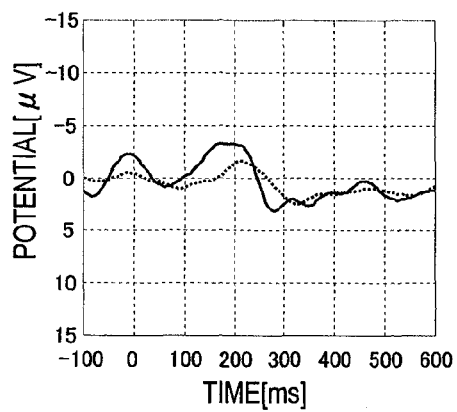
(a) CONDITION ML
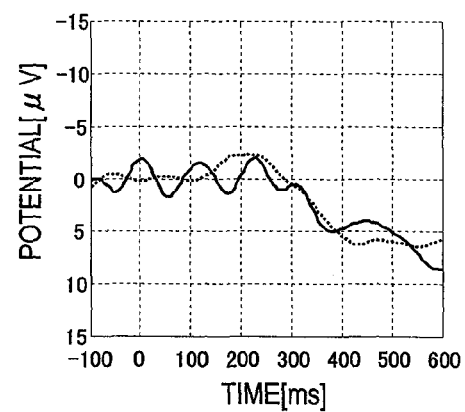
(b) CONDITION MM
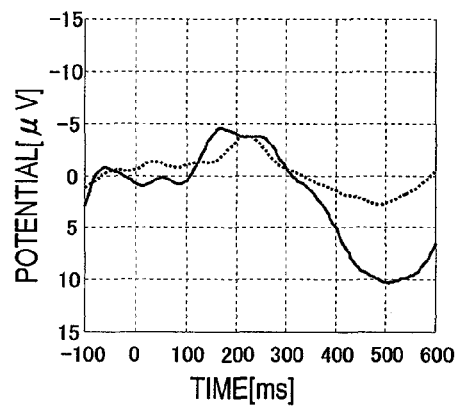
(c) CONDITION MH

FIG.6
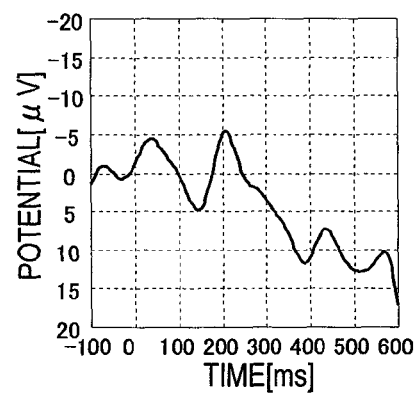
(a) CONDITION ML
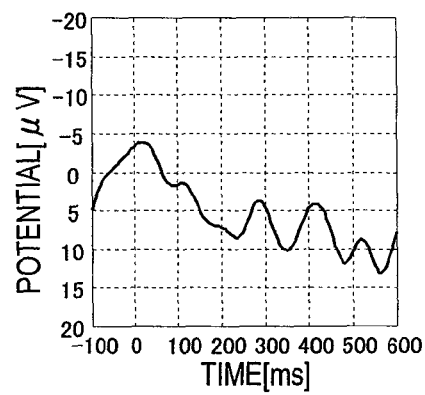
(b) CONDITION MM
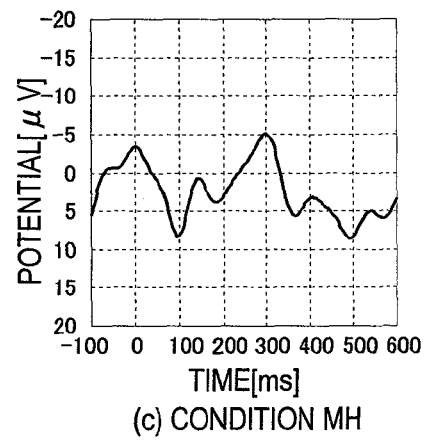
(c) CONDITION MH

FIG. 7

| EXPERIMENTAL CONDITIONS | | AROUSAL LEVEL (α WAVE INTENSITY) | | ATTENTION ALLOCATION TO TASK OTHER THAN DRIVING | | RESULT OF DETERMINATION BASED ONLY ON ATTENTION ALLOCATION | | RESULT OF DETERMINATION WHICH ALSO TAKES AROUSAL LEVEL INTO CONSIDERATION | |
|---|---|---|---|---|---|---|---|---|---|
| DRIVING | OTHER THAN DRIVING | | | AMPLITUDE (μV) | CLASSIFY | ESTIMATE DRIVING ATTENTION | RESULT OF ASSISTANCE | ESTIMATE ATTENTION | RESULT OF DETERMINATION |
| LOW | LOW | 0.264 | L | 0.67 | L | H | - | 0.7 | DISTRACTED |
| MEDIUM | LOW | 0.706 | M | 1.08 | L | H | - | 1.4 | - |
| HIGH | LOW | 0.744 | M | -1.39 | L | H | - | 1.6 | - |
| LOW | MEDIUM | 0.322 | L | 8.24 | H | L | DISTRACTED | 0.1 | DROWSY |
| MEDIUM | MEDIUM | 0.785 | M | 2.39 | M | M | DISTRACTED | 0.8 | DISTRACTED |
| HIGH | MEDIUM | 1.445 | H | 0.35 | L | H | - | 2.1 | - |
| LOW | HIGH | 0.171 | L | 7.00 | H | L | DISTRACTED | 0.1 | DROWSY |
| MEDIUM | HIGH | 0.738 | M | 2.50 | M | M | DISTRACTED | 0.8 | DISTRACTED |
| HIGH | HIGH | 0.679 | M | 0.76 | L | H | - | 1.4 | - |

FIG.17

| EXTERNAL ENVIRONMENT | | | | REQUIRED AMOUNT OF ATTENTION |
|---|---|---|---|---|
| TIME ZONE/ILLUMINANCE | ROAD SURFACE SITUATION | WEATHER | NUMBER OF OBJECTS REQUIRING ATTENTION | |
| 12:00 (BRIGHT) | DRY | FINE | FEW (0-1) | SMALL |
| 14:00 | WET | RAINY | FEW (0-1) | MEDIUM |
| 18:00 | DRY | FINE | MANY (5 OR MORE) | LARGE |
| 23:00 | FROZEN | SNOWY | FEW (0-1) | VERY LARGE |
| ... | ... | ... | ... | ... |
| 40 | 41 | 42 | 43 | 44 |

DISTRACTION DETECTION APPARATUS, DISTRACTION DETECTION METHOD, AND COMPUTER PROGRAM

This is a continuation of International Application No. PCT/JP2009/004771, with an international filing date of Sep. 18, 2009, which claims priority of Japanese Patent Application No. 2008-240470, filed on Sep. 19, 2008, the contents of which are hereby incorporated by reference.

BACKGROUND OF THE INVENTION

1. Field of the Invention

The present invention relates to a device for providing assistance in safe driving by measuring the state of a driver by utilizing an electroencephalogram.

2. Description of the Related Art

In recent years, in connection with accident prevention apparatuses related to automobile driving, methods of measuring a state of a driver and providing driving assistance based on the result of measurement have been under study.

Methods of inferring the state of a driver include an indirect method of acquiring a steering angle, changes in traveling velocity, and the like, which reflect the manner in which an automobile is being operated. With information that is easy to acquire from the device side, in combination with white line detection, for example, this method has enabled assistance such as evaluating driving stability.

There are also methods which directly measure a driver's state, rather than a vehicle's state. For example, there have been attempts of detecting a driver's act of looking aside or drowsiness by detecting the direction of the line of sight or the status of blinking with a camera which is aimed at the driver, for example.

Furthermore, as a method of directly measuring a driver's state, a method of measuring an electroencephalogram of the driver is possible. An electroencephalogram, which is a potential change on the scalp that is measurable of the head, is supposed to reflect encephalic activities, and may possibly be an optimum representation of a driver's state.

The present invention aims to provide a distraction detection apparatus concerning the driving of a driver. An attention status during the driving of a driver is one of the statuses that are difficult to establish from the vehicle status, e.g., steering angle, or from external measurements with a camera, for example. Thus, it is considered that detection of a distracted status can serve as effective information for assistance in safe driving.

An example of an existing application concerning attention detection is an invention disclosed in Japanese Laid-Open Patent Publication No. 2004-178367 (hereinafter referred to as "Patent Document 1"), for example. This is an invention of detecting attention allocation of a driver from the vehicle status and from the line of sight or face motion of a driver.

An invention disclosed in Japanese Laid-Open Patent Publication No. 2005-228003 (hereinafter referred to as "Patent Document 2") is directed to a method where, by using a database previously storing a relationship between the brain activity status and the vehicle operation of a driver, activities within the brain are estimated from the behavior of a vehicle. Encephalic activities are estimated from vehicle operating information.

However, with Patent Document 1 above, it is difficult to cope with the type of distracted situation where the line of sight is aimed but attention is absent, for example.

According to Patent Document 2, since there is no one-to-one correspondence between the behavior of a vehicle and activities within the brain, it is believed that some ambiguity will be left in the result of estimation. For example, when a relatively slow braking operation occurs, it is impossible to distinguish whether the driver was thinking that there was enough leeway or the driver was driving absent-mindedly, unless measurements were taken of the driver at that point in time.

Thus, in the detection of distraction, more accurate measurement methods have been desired.

SUMMARY OF THE INVENTION

The present invention has been made in order to solve the aforementioned problems, and an objective thereof is to accurately detect whether a driver is being distracted or not, and provide appropriate assistance in safe driving for the driver.

A distraction detection apparatus according to the present invention comprises: an electroencephalogram detection section for detecting an electroencephalogram signal of a driver; an arousal level estimation section for retaining a first rule of mapping parameter values of an electroencephalogram signal to arousal levels, and estimating an arousal level based on the detected electroencephalogram signal and the first rule; an attention allocation estimation section for retaining a second rule of mapping parameter values of an electroencephalogram signal to attention allocations, and estimating an attention allocation based on the detected electroencephalogram signal and the second rule; a driver state estimation section for retaining a third rule of deriving an amount of attention from an arousal level and an attention allocation, estimating an amount of attention of the driver paid to driving based on the estimated arousal level and attention allocation and the third rule, and classifying a state of the driver into a normal state, a state of reduced attention, or a state of reduced arousal level; and an output section for performing an intervention for the driver based on a result of classification by the driver state classification section.

The first rule may map frequency intensities of an electroencephalogram signal to arousal levels; and the arousal level estimation section may calculate a frequency intensity of the detected electroencephalogram signal, and estimate the arousal level based on a result of calculation and the first rule.

A plurality of groups may be previously defined in the arousal level estimation section, each group being defined based on a frequency intensity of an electroencephalogram signal; and the arousal level estimation section may classify frequency intensities of the detected electroencephalogram signal as calculated at a plurality of points in time, each frequency intensity being classified into one of the plurality of groups, and estimate the arousal level based on at least one frequency intensity that is classified into one of the plurality of groups and on the first rule.

The second rule may map amplitudes of event-related potentials of an electroencephalogram signal to attention allocations; and the attention allocation estimation section may calculate an amplitude of an event-related potential of the detected electroencephalogram signal, and estimate the attention allocation based on a result of calculation and the second rule.

A plurality of groups may be previously defined in the attention allocation estimation section, each group being defined based on an amplitude of an event-related potential; and the attention allocation estimation section may classify amplitudes of the event-related potential of the detected electroencephalogram signal as calculated at a plurality of points in time, each amplitude of the event-related potential being classified into one of the plurality of groups, and estimate the attention allocation based on at least one amplitude of the event-related potential that is classified into one of the plurality of groups and on the second rule.

The distraction detection apparatus may further comprise an external environment detection section for detecting an external environment, wherein the driver state estimation section may have a rule of deriving a required amount of attention based on a detected external environment, and compare the amount of attention paid to driving as estimated by the driver state estimation section against a required amount of attention derived by applying the rule to the external environment detected by the external environment detection section, thus determining whether the driver is paying attention to complexity in the external environment.

The driver state estimation section may calculate an amount of attention of the driver paid to driving by multiplying the arousal level estimated by the arousal level estimation section and an attention allocation to driving estimated by the attention allocation estimation section.

The attention allocation estimation section may have a rule defining a relationship between an attention allocation to a task other than driving and an attention allocation to driving, and be capable of estimating an attention allocation to driving based on an attention allocation to the task other than driving and the rule; and the driver state estimation section may calculate an amount of attention of the driver paid to driving by multiplying the arousal level estimated by the arousal level estimation section and the attention allocation to driving estimated by the attention allocation estimation section.

A distraction detection method according to the present invention comprises the steps of: providing a first rule of mapping parameter values of an electroencephalogram signal to arousal levels; providing a second rule of mapping parameter values of an electroencephalogram signal to attention allocations; providing a third rule of deriving an amount of attention from an arousal level and an attention allocation; detecting an electroencephalogram signal of a driver; estimating an arousal level based on the detected electroencephalogram signal and the first rule; estimating an attention allocation based on the detected electroencephalogram signal and the second rule; estimating an amount of attention of the driver paid to driving based on the estimated arousal level and attention allocation and the third rule, and classifying a state of the driver into a normal state, a state of reduced attention, or a state of reduced arousal level; and performing an intervention for the driver based on a result of classification by the classifying step.

A computer program stored on a non-transitory computer-readable medium according to the present invention is executed by a computer and causes the computer to execute the steps of: receiving an electroencephalogram signal of a driver; estimating an arousal level based on the detected electroencephalogram signal of the driver and a first rule of mapping parameter values of an electroencephalogram signal to arousal levels; estimating an attention allocation based on the detected electroencephalogram signal and a second rule of mapping parameter values of an electroencephalogram signal to attention allocations; estimating an amount of attention of the driver paid to driving based on the estimated arousal level and attention allocation and a third rule of deriving an amount of attention from an arousal level and an attention allocation, and classifying a state of the driver into a normal state, a state of reduced attention, or a state of reduced arousal level; and performing an intervention for the driver based on a result of classification by the classifying step.

With a distraction detection apparatus according to the present invention, a driver's state can be more accurately determined with only an electroencephalogram sensor, whereby an appropriate assistance which is suited to the state can be provided. Moreover, because the device provides appropriate assistance for the driver, the user's trust will increase, thus enabling the driver to appropriately respond to information from the device. As a result, safe driving can be realized.

Other features, elements, processes, steps, characteristics and advantages of the present invention will become more apparent from the following detailed description of preferred embodiments of the present invention with reference to the attached drawings.

BRIEF DESCRIPTION OF THE DRAWINGS

Portion (a) of FIG. 1 is a diagram showing an exemplary determination method; and Portion (b) of FIG. 1 is a diagram showing an exemplary determination method which combines arousal level determination and attention allocation determination.

FIG. 2 is a diagram showing how difficulty levels may be set with respect to tasks.

FIG. 5 is a diagram showing some of the experimental results of FIG. 4 as waveforms.

FIG. 6 is a diagram showing, in a driving task of following a preceding car, exemplary graphs obtained by taking an average of event-related potentials based on activation of brake lamps of the preceding car as a starting point.

FIG. 7 is a diagram showing results of attention determination.

FIG. 17 is a table storing some factors governing an external situation, and required amounts of attention corresponding thereto.

DETAILED DESCRIPTION OF PREFERRED EMBODIMENTS

Figure 3:
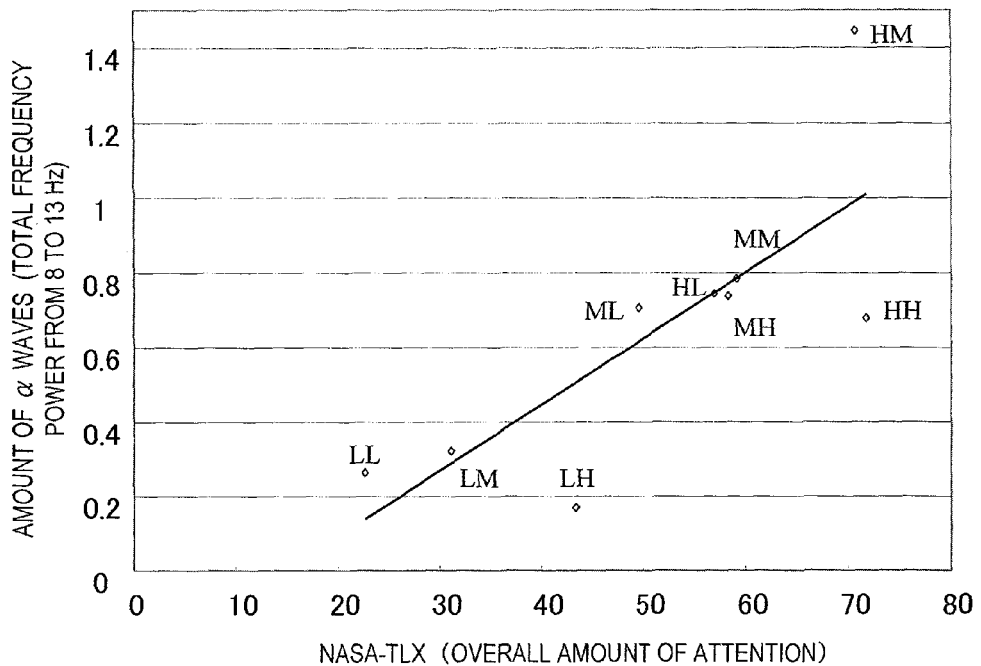
FIG. 3 is a diagram showing experimental results concerning arousal levels.

Prior to describing Embodiments of the present invention, experiments which have been performed by the inventors will be described first. Then, findings of the inventors which have been derived from the results of the experiments will be described.

The inventors have paid attention to an electroencephalogram, which permits measurement of encephalic activities with a good response time and a high time resolution, and studied its availability for detection of distraction.

One field of electroencephalogram studies is attention studies. For example, "Measuring attention to video clips: An application of the probe stimulus technique using event-related brain potentials" (Nittono, Japanese Journal of Physiological Psychology and Psychophysiology, 2006, 24(1), 5-18) describes a method of measuring attention allocation from an event-related potential which is measured based on the timing of video presentation as a starting point, by using a probe stimulus technique.

As used herein, a "probe stimulus technique" is a method of setting two tasks, i.e., a primary task and a secondary task, and estimating the attention allocation for the primary task based on the attention allocation for the secondary task. Moreover, an "event-related potential" refers to a transient potential fluctuation in the brain which occurs in temporal relationship with an external or internal event. In this document, an electroencephalogram near 300 ms based on the timing of video presentation as a starting point is cut out, and information is read from the waveform shape (amplitude) of that electroencephalogram. This electroencephalogram component is referred to as a P300 component of the event-related potential.

The inventors have thought that, by applying the above knowledge to a driving scene, it becomes possible to measure attention allocation via an electroencephalogram. Then, based on the hypothesis that the amount of attention to driving is estimable from the attention allocation for a task other than driving, an experiment using a driving simulator was performed, and its effectiveness was confirmed.

However, it has been found that attention allocation alone does not suffice because there exist two possible cases of insufficiency of attention during driving: distraction due to paying attention to tasks other than driving; and there being less than enough attention due to overall drowsiness. These two cases must be separated in order to provide appropriate driving assistance.

Moreover, studies of attention allocation stand on the premise that the arousal level of the test subject is at the maximum. When this premise is true, attention to a primary task can be estimated from the attention allocation for a secondary task. However, a maximum arousal level is not always the case in driving scenes.

These tasks will be described based on case instances. A similar notion to attention detection is arousal level detection, which is substantially synonymous to detection of drowsiness. A decrease in the arousal level is considered to indicate strong drowsiness. For example, Japanese Laid-Open Patent Publication No. 2007-000280 discloses a method of determining a decrease in the arousal level based on an electroencephalogram. If detection of a decrease in the arousal level and detection of a decrease in the amount of attention were independently made, wrong information may be presented to the driver.

FIG. 1(a) shows an exemplary determination method. In this case, based on the amplitude being large or small with respect to a task other than driving, which correspond to probe stimuli, it is determined as to whether attention is sufficient or not.

However, this determination alone does not support the case where, in spite of a large attention allocation, a low arousal level still renders the amount of attention insufficient, and the case where, in spite of a small attention allocation, a high overall arousal level eliminates problems.

Thus, when arousal level determination and attention determination operations are independently performed, there will be an increased possibility of making a determination which does not correctly reflect the driver's state. A safe driving assistance system which incorporates such a determination apparatus will not operate appropriately, and therefore the driver's trust therein will decrease. The trust of a driver in a safe driving assistance system is an important attribute which affects the driver's ability to appropriately act when an alarm to the driver is truly needed.

In connection therewith, Japanese Laid-Open Patent Publication No. 2007-265377 discloses a driver state determination apparatus in which an arousal level, a degree of attention and concentration, and driver information reflecting driving ability are utilized. The arousal level is detected from an electroencephalogram, a heart rate state, a rate of eye-closed time, a facial expression drowsiness value, and the like. The degree of attention and concentration is determined from a head acceleration, a head image, a cervical electromyogram, and the like. This document states that a plurality of states of a driver can be distinguished based on a combination of them. However, it is necessary to introduce a plurality of sensors respectively corresponding to the plurality of pieces of information to be detected. Moreover, heart rate detection with a heart rate meter, facial expression detection with a camera, and motion detection with an acceleration sensor can only indirectly reflect the state of a driver's attention. For example, with a camera and an acceleration sensor alone, it is difficult to accurately detect drowsiness and attention at present.

Therefore, the inventors have studied a method of, given the current arousal level of a driver, integratively determining how much attention the driver allocates to driving, thus more accurately estimating the driver's state. Specifically, the inventors have studied whether a driver's state can be estimated more accurately and easily by only using an electroencephalogram sensor, which is considered to most directly reflect a driver's state, to integratively determine both an arousal level and a degree of attention and concentration respectively with different analysis methods.

FIG. 1(b) shows an exemplary determination method in which arousal level determination and attention allocation determination are combined. This is characterized in that it is possible to determine a case of a large attention allocation but a low arousal level state (cell 11) and a case of a small attention allocation but a high overall arousal level which eliminates problems (cell 12), with only an electroencephalogram.

The inventors have conducted an experiment using a driving simulator. The experiment was performed by applying double tasks as follows to the situation during driving, based on the concept of the probe stimulus technique described in the aforementioned document.

First, as a task concerning driving, a driver riding on a driving simulator was asked to perform a task of following a preceding car which was displayed on a screen, while trying to maintain a constant vehicular gap of 20 to 30 m therefrom. In a task of following a preceding car, it is necessary to drive in response the braking operations or accelerations of the preceding car.

As a task other than driving (corresponding to a secondary task in the probe stimulus technique; hereinafter a "non-driving task"), a display-viewing task was imposed, which involved pressing a button on the steering wheel in response to a specific direction (which was the right arrow in this experiment) among up/down/right/left arrows being indicated on a display which was provided on the dashboard of the driving simulator. This contemplates a task where a car navigation system designates a direction, and the driver manipulates a button when information of a restaurant or a gas station is presented. Too large an attention to such a task other than driving is associated with less than sufficient attention allocation for driving.

For each of such double tasks, in order to introduce an experimental variation in attention allocation during driving, the difficulty level was varied in three levels. Specifically, as for the driving task, the speed of the preceding car was varied; and as for the non-driving task, the interval with which arrows designating directions were indicated was varied.

Under this setting, based on the concept of the probe stimulus technique, an event-related potential while a non-driving task was being performed was acquired, and by using the amplitude thereof, an amount of allocated attention for the non-driving task was first determined, and thereafter an amount of allocated attention for driving was determined.

The experiment involved a measurement experiment for eight test subjects who were in their thirties to forties, and the electroencephalogram data of six people, excluding the two who were unable to successfully perform the task of following a preceding car, was subjected to analysis.

As for the electroencephalogram measurement, Polymate AP-112 (manufactured by DIGITEX LAB. CO., LTD) was used, and a measuring electrode was worn at Pz (according to the position notation of the International 10-20 system, the same will similarly apply below), a reference electrode was worn at A1 (right earlobe), and the ground electrode was worn at FPz (metopic). The sampling frequency was 200 Hz; the time constant was 3 seconds; and a 30 Hz low-pass filter was used for filtering.

FIG. 2 shows how difficulty levels may be set with respect to tasks, concerning difficulty levels of experimental tasks. Three difficulty levels were independently set for a driving task as a primary task and a non-driving task (display-viewing task) as a secondary task, such that the experiment was performed with respect to nine different attention allocation situations by executing all three combinations of situations.

The course on the driving simulator contemplated a situation where a preceding car was moving on an expressway course. Since the preceding car kept moving with acceleration or braking, a driving of following in response to the motion of the preceding car was required. One trial took about 5 minutes.

First, FIG. 3 shows experimental results concerning arousal levels. The vertical axis represents an α wave band (indicating a total intensity value of frequencies from 8 to 13 Hz), and the horizontal axis represents an evaluation value of a subjective workload of NASA-TLX psychological workload. "NASA-TLX" is a Task Load Index developed at Ames Research Center of NASA, which is considered as an index that enables an evaluation of mental load. Correlation with this index was checked as an index as to how well an arousal level is estimable from an electroencephalogram.

The two alphabetical letters attached to each plot are an indication of experimental conditions. The first letter indicates a difficulty level as to the driving task. The second letter indicates a difficulty level as to the non-driving task (display-viewing task). In each, L/M/H indicate low, medium, and high difficulty levels, respectively. With a combination of these two letters, it is possible to know what intensity has been observed in which situation.

As indicated by a correlation coefficient of 0.78, it can be seen from FIG. 3 that the intensity of α waves is correlated with the NASA-TLX subjective workload, so that a value corresponding to the arousal level is estimable through a frequency analysis of the electroencephalogram.

Figure 4:
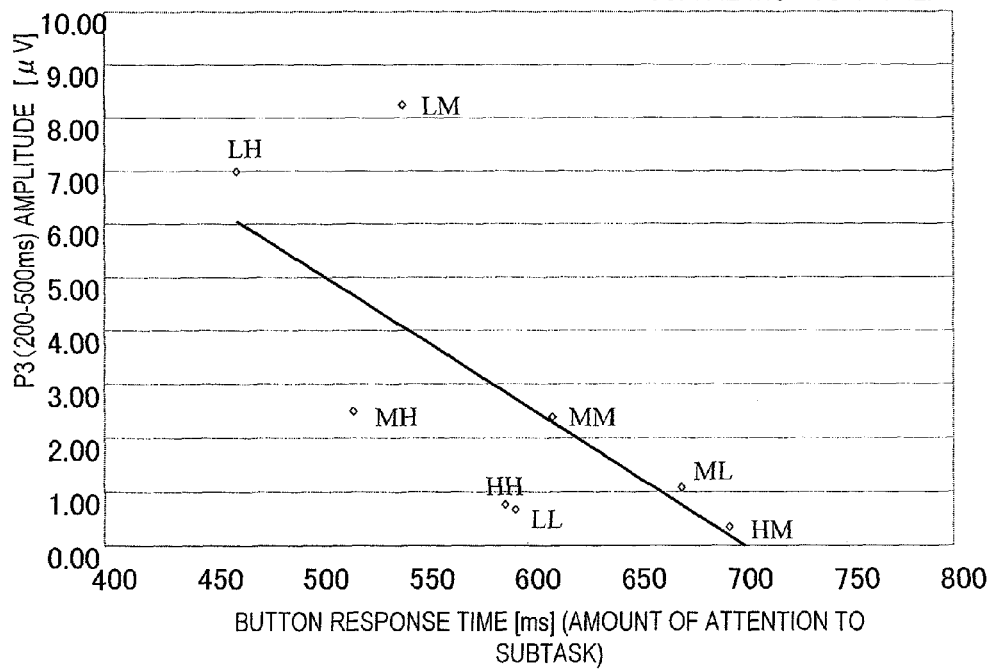
FIG. 4 is a diagram showing experimental results concerning attention allocation.

Next, FIG. 4 shows experimental results concerning attention allocation. The vertical axis represents a plotting of the P3 maximum amplitude in a zone from 200 to 500 ms. Again, for reference, a correlation with the button response time is shown, the correlation coefficient being—0.77. It can be said that attention allocation is exhibited in the amplitude of the event-related potential. A short button response time is considered to indicate sufficient attention being directed. Thus, since there is correlation between response time and amplitude, it can be seen that amplitude is also an effective index of attention allocation.

Next, FIG. 5 shows some of the experimental results of FIG. 4 as waveforms. The experimental conditions were: (a) condition ML, (b) condition MM, and (c) condition MH. The difficulty level of the driving task was fixed at medium (M), while the non-driving task (display-viewing task) was varied among difficulty levels L, M, and H. The horizontal axis of each graph represents elapsed time since the timing of activating a stimulation (arrow) presented on the display in units of ms, whereas the vertical axis represents potential of the electroencephalogram in units of μV. In each graph, two lines are drawn: a solid line indicating response to a stimulation of a specific direction (which is the right arrow in this experiment) that requires pressing of the button in the display-viewing task; and a broken line indicating response to a stimulation that does not require pressing of the button. It can be seen from FIG. 5, in response to display viewing, there is a potential change with a positive peak from 400 to 500 ms, which is presumably a kind of P300, and its amplitude level increases as the display-viewing task becomes more difficult (as from (a) to (c) in FIG. 5). Presumably, this change in amplitude is in relation to the quantity of attention allocation for the non-driving task (display-viewing task).

Next, other than the results of FIG. 4, results of measuring the amount of allocated attention for driving will be described. FIG. 6 shows, in a driving task of following a preceding car, exemplary graphs obtained by taking an average of event-related potentials based on activation of brake lamps of the preceding car as a starting point. The experimental conditions are the same as in FIG. 5. That is, (a) condition ML, (b) condition MM, and (c) condition MH were employed; the difficulty level of the driving task was fixed at medium (M); and the non-driving task (display-viewing task) was varied among difficulty levels L, M, and H. In each graph, the horizontal axis represents elapsed time since the timing of activating the brake lamps of the preceding car in units of ms, whereas the vertical axis represents potential of the electroencephalogram in units of μV. In FIG. 6, as the non-driving task becomes more difficult, the amount of attention paid to driving becomes more decreased. Therefore, it is expected that the amount of attention paid to driving is smaller and the amplitude will also be smaller under the condition MH than under the condition ML, for example. However, although there is a tendency of decreasing amplitude, no positive potential change that is as clear as that of P300 in FIG. 5 is observed.

Thus, it has been indicated that there is a difference in the likelihood of appearance of P300, between the event-related potential for the task other than driving (FIG. 5) and the event-related potential for the driving task (FIG. 6). The reason is as follows. The event-related potential for the task other than driving was measured with respect to a display-viewing task, i.e., under conditions where controlled stimulations were presented on a display which was set within the car. On the other hand, as for the event-related potential with respect to the driving task, the brake lamps of the preceding car may have a clear starting point, but did not necessary provide for stable viewing conditions.

The reason is that, although the participants were instructed to drive while keeping the distance from the preceding car as constant as possible, there were many time periods when this condition was not satisfied because the preceding car repeated deceleration and acceleration. As a result, the visual stimulations based on activations of the brake lamps, which would be lit either far or near depending on the distance from the preceding car, were inconstant. Moreover, it was not always the case that the preceding car was being watched at the moments when the brake lamps were activated because, under the experimental conditions, the display-viewing task was imposed in addition to the driving task, and also the steering operation had to be performed in response to the road surface situation other than the preceding car in the driving screen. Thus, presumably, a stable positive component was not observed because the stimulations were inconstant and the timing of viewing stimulations was inconstant.

An event-related potential with respect to driving is considered to be measurable with respect to various events occurring outside the car. However, even apart from the above case instance concerning the brake lamps of a preceding car, it is expectable that events outside the car are likely to fluctuate in terms of the level and timing of stimulations, thus making it difficult to directly and stably measure an event-related potential with respect to driving. From this finding, it can be said that at least the visual stimulations and audio stimulations which are generated by a device within the car are stable, and so are the event-related potentials in response thereto. Thus, it will be easier for a device for detecting the state of a driver to achieve a stable operation with an event (task other than driving) that is generated by a device within the car as a starting point.

Results of performing an attention determination based on the above experimental results will be described. FIG. 7 shows results of attention determination. In FIG. 7, in this order from the leftmost, experimental conditions, estimated values of arousal levels, estimated values of attention allocation for the non-driving task, and the results of determination are shown.

FIG. 7 produces the conclusion that stable attention determination is possible, without being influenced by minute numerical differences, by grouping numerical data by taking into consideration not only attention allocation for a task other than driving, but also an arousal level which is calculated from the electroencephalogram. This will be described in detail below.

In FIG. 7, the experimental conditions are represented by a required amount of attention 20 for driving and a required amount of attention 21 for the task other than driving. Herein, the required amounts of attention were the three of high, medium, and low, respectively corresponding to the difficulties of tasks shown in FIG. 2. Through various combinations between the required amount of attention 20 for driving and the required amount of attention 21 for the task other than driving, states corresponding to a state of being distracted and a drowsy state are evoked.

A column 22 indicates an arousal level (intensity of α waves) corresponding to each experimental condition, these values being obtained by extracting intensities of α waves from the analysis results shown in FIG. 7. A column 23 indicates results of classifying these values into the three groups of L, M, and H. The method of classification into groups is based on three arbitrary intensity ranges of α waves.

Classification can be performed by designating 0.5 or less as L, 0.9 or more as H, and anything in between as M, for example.

Columns 24 and 25 indicate results of attention allocation for the task other than driving, which is another piece of information in addition to the arousal level. The column 24 is obtained by extracting the amplitude of an event-related potential corresponding to each condition from FIG. 4. Similarly, the column 25 indicates results of classifying the values of the column 24 into the three groups of L, M, and H. Similarly, the threshold values for the grouping can be set from FIG. 4. The column 25 represents classification from numerical intensities corresponding to the respective conditions of FIG. 7, for example, 2.0 or less may be designated as L, 5.0 or more as H, and anything in between as M.

Columns 26 and 27 indicate results of attention determination for driving, in the case of only utilizing attention allocation for the task other than driving. It is assumed that the attention allocation for driving is determined as a remainder of attention after it is allocated to the task other than driving. For example, if the attention allocation for the task other than driving is L, M, or H, then the attention allocation for driving can be mapped to H, M, or L, respectively. The column 26 indicates mapping of attention allocation. By defining "L" or "M" attention to driving as being distracted, it becomes possible to determine distraction under fixed criteria.

On the other hand, columns 28 and 29 indicate results of determining attention allocation by also taking the arousal level into consideration. These results of determination were calculated from the following equation.

Amount of attention to driving=intensity of α waves*
(1− amplitude of event-related potential with
respect to task other than driving)

In the above equation, as for the intensity of α waves, values "1", "2", and "3" were used corresponding to the grouping of L, M, and H (column 23), respectively. Moreover, as for the amplitude for an event-related potential with respect to the task other than driving (Event Related Potential; ERP), values "0.3", "0.6", and "0.9" were used corresponding to the grouping of L, M, and H (column 25), respectively. Thus, by introducing discretization processes, i.e., grouping, there is provided an effect of obtaining stable results of determination.

A column 28 indicates values which are calculated based on the above equation. These are results of determination which take the arousal level also into consideration. Therefore, depending on the sizes of the values, they can be classified into "drowsy", "distracted", and "normal", in ascending order. Although the threshold values thereof may be modified depending on the actual data, 0.5 or less may be classified as "drowsy", 0.5 to 1.0 "distracted", and 1.0 or more as "normal", for example.

For example, through a determination based only on attention allocation, a row 31 will be determined as indicating that sufficient attention is being paid to driving. However, in actuality, this is a situation where no attention is being paid to either driving or the task other than driving. Through a combination with the arousal level, this situation is determined as a case of being distracted (column 29). In the case instances of rows 32 and 33, the low arousal level itself affects the final values, thus resulting in the determinations of "drowsy" rather than "distracted".

Thus, by introducing a plurality of discretization processes for electroencephalogram measurement values, it becomes possible to estimate a driver's state from characteristics which are obtained through signal processing of the electroencephalogram. Moreover, as can be seen from FIG. 7, there is a possibility that a state of being distracted and a state of strong drowsiness can be distinguished through a combination with the arousal level, as opposed to the dichotomous determination as to sufficiency of attention which is enabled by the determination based only on attention allocation.

Thus it has been indicated that a distinction can be made between drowsiness and distraction in a situation of driving a driving simulator, by estimating an arousal level through frequency analysis of an electroencephalogram, estimating an attention allocation through event-related potential analysis of the electroencephalogram, and making an integrative determination of these.

Note that, as for the intensity of α waves and the amplitude of event-related potential, their measured/calculated values do not directly correspond to arousal levels and amounts of allocated attention, but they need to be subjected to a certain degree of classification. By grouping these nine kinds of experiment data, instability of the measurement results can be eliminated, and stable results can be obtained, for example.

For example, from the present data distribution, border lines may be set with specific groups in mind; e.g., L<0.5<M<1.0<H may be set for arousal levels, and L<2.0<M<5.0<H may be set for attention allocation.

Based on the above findings, there will be described a construction and processing for distinguishing whether a driver is paying sufficient attention to driving or not based on an electroencephalogram, and classifying insufficient attention into a state of strong drowsiness or a state of being distracted, and providing assistance according to the state.

Hereinafter, with reference to the attached drawings, embodiments of the present invention will be described.

(Embodiment 1)

Figure 8:
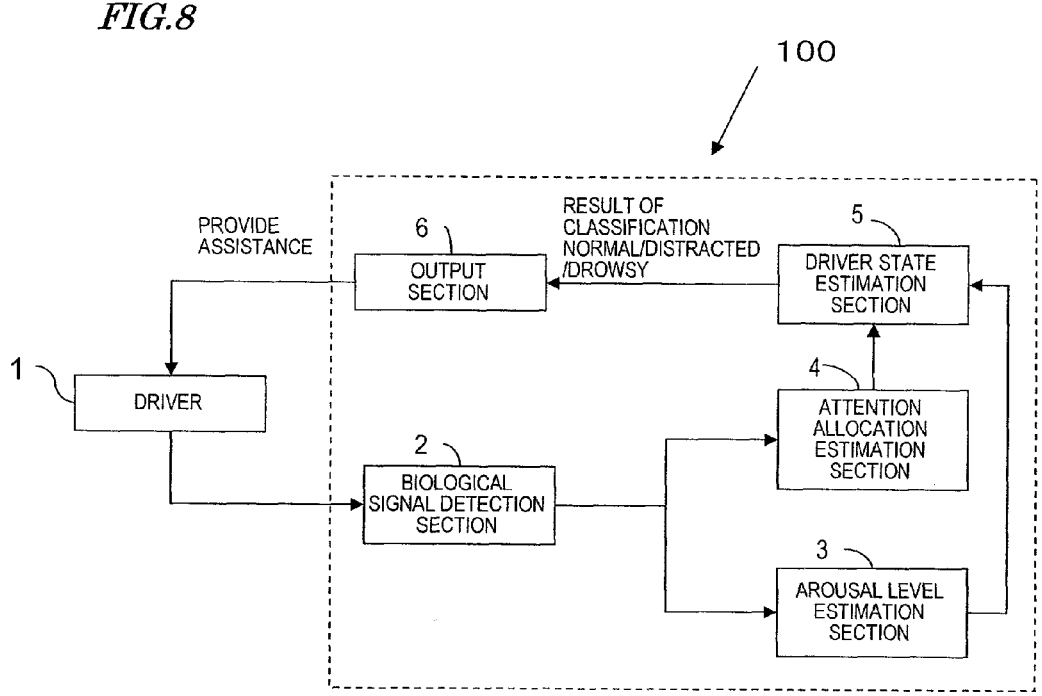
FIG. 8 is a construction diagram showing a distraction detection apparatus 100 according to Embodiment 1.

FIG. 8 is a construction diagram of a distraction detection apparatus 100 according to Embodiment 1 of the present invention. The distraction detection apparatus 100 includes a biological signal detection section 2, an arousal level estimation section 3, an attention allocation estimation section 4, a driver state estimation section 5, and an output section 6.

The biological signal detection section 2 measures an electroencephalogram of a driver 1. The biological signal detection section 2 is an electroencephalograph, for example.

The arousal level estimation section 3 estimates an arousal level of the driver by analyzing the measured electroencephalogram signal. The "arousal level" is an index indicating how clear the consciousness of the driver is, such that the arousal level decreases as the driver becomes drowsy. An estimation of the arousal level serves as an index which is highly related to how drowsy the driver is.

The attention allocation estimation section 4 estimates an amount of allocated attention by analyzing the measured electroencephalogram signal with another method. As used herein, "attention allocation" is an index which indicates, within the total amount of attention that a driver can afford, how much attention is allocated to a given task. The method with which the attention allocation estimation section 4 estimates an amount of allocated attention will be described later.

Moreover, based on the results of estimation from the arousal level estimation section 3 and the amount of attention estimation section 4, the driver state estimation section 5 classifies the driver's current state. A "driver's state" refers to a state concerning attention, among various states of the driver, and is divided into the three following states in the present specification. A driver's state is classified into one of these three states:

state A: sufficient attention is being paid to driving;
state B: the arousal level is sufficient, but sufficient attention is not being paid to driving; and
state C: since the arousal level is low, attention to driving is not enough.

The arousal level estimation section 3, the attention allocation estimation section 4, and the driver state estimation section 5 may be implemented as dedicated semiconductor chip circuits for realizing the respective functions, for example.

Based on the result of classification by the driver state estimation section 5, the output section 6 outputs information with which to call the attention of the driver, or the like. The output section 6 is a loudspeaker which calls out to the driver with an audio, or presents an operating sound or an alarm sound, for example. Alternatively, the output section 6 may present text or images on a car navigation system or a head-up display. Otherwise, direct presentation of information using an AR (Augmented Reality) technique, which involves displaying in the form of an overlay on an object which needs attention, attention calling through a vibration of the steering wheel or the like, an indirect intervention through a smell or adjustment of an amount of fanned air, and the like, are also encompassed.

Hereinafter, among the notions which pertain to the present embodiment, the notion of "attention allocation" as used in the attention allocation estimation section 4 and the like, and a distinction between a "state of distraction" and "drowsiness" will be described.

"Attention allocation" indicates, among the various tasks which are performed by a driver who is driving an automobile, how much attention is allocated to which task. "Attention" is a psychological quantity which is consciously directed to the confirmation of a certain state of an object or execution of a task. Attentive driving is required for safe driving.

The driver who is driving an automobile is performing various tasks. Examples thereof include driving-related tasks, e.g., confirmation of safety in the front, confirmation of traffic lights, and paying attention to movements of pedestrians and bicycles, and also tasks which are not directly related to driving, e.g., listening to music, operations of a car navigation system or a car stereo, acquisition of information from the radio or the like, and conversations with someone in the car. Regarding these tasks, the driver is presumably performing a plurality of tasks concurrently, while altering the allocation of attention in various manners depending on each situation and the like.

Among these tasks, if attention to driving is less than sufficient, there may be cases where it will be effective for a device to call attention to driving because otherwise adequately safe driving would not be attained. For example, when attention allocation to a situation occurring at the vehicle front is low because of being absorbed in a chat with someone in the car, the ability to cope with abrupt changes in the situation will be reduced. Also, in the case of strong drowsiness, actions will be delayed with respect to changes in the situation. Now, the former case instance of being engaged in a conversation, where attention to driving is reduced although a sufficient arousal level exists, and the latter case instance of reduced attention due to a strong drowsiness should be dealt with by different methods, even though they both fall short of safe driving. It is a concept of the present invention to distinguish between these cases and handle them differently.

Figure 9:
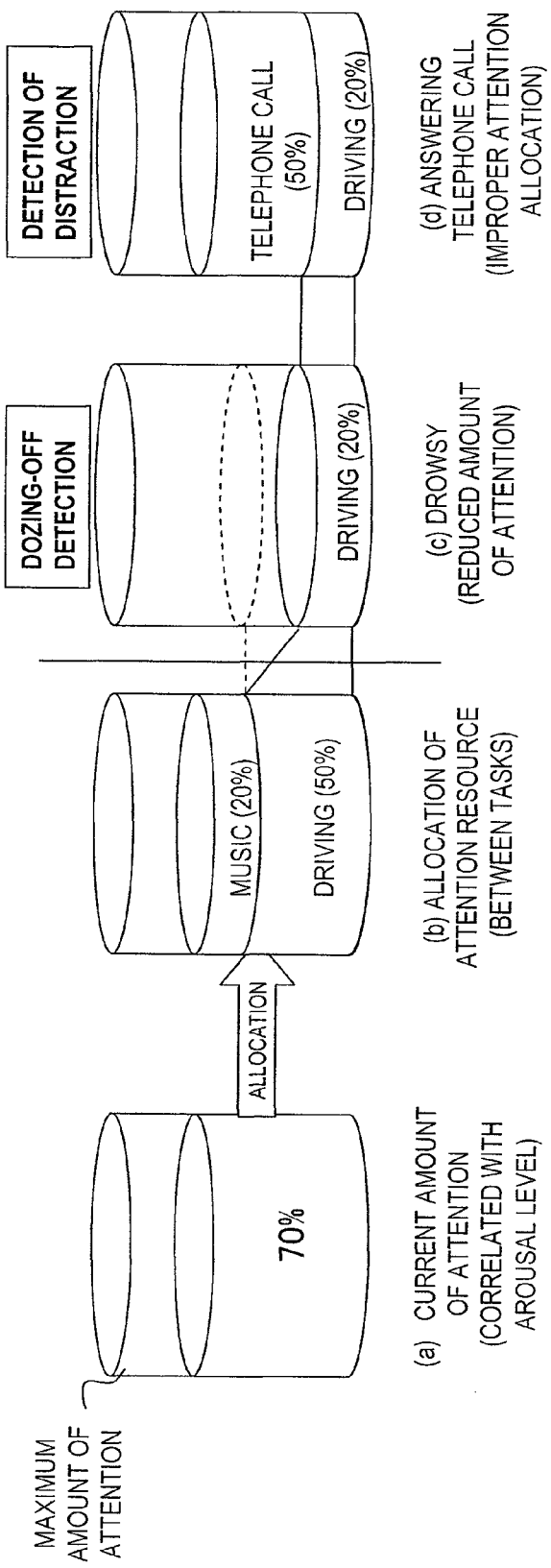
FIG. 9 is a diagram describing allocation of amounts of attention.

Allocation of amounts of attention will be further described with reference to FIG. 9. The present invention employs the notion of "quantity" with respect to attention.

More specifically, as shown in FIG. 9(a), a current amount of attention may be regarded as a quantity, as of water which is stored in a cylinder. The size of the cylinder is the maximum amount of attention that the driver can afford. The stored water corresponds to the actual attention, which quantity is considered to increase or decrease depending on the degree of concentration or the arousal level. For example, in the case of FIG. 9(a), it is assumed that there is an amount of attention of 70%. This value is conveniently selected for explaining the notion of attention allocation. This amount of attention is to be allocated among tasks which are performed by the driver at each moment. In FIG. 9(b), during a driving while listening to music, for example, 50% of the entire attention may be allocated to driving, whereas 20% of the attention may be allocated to music. It is assumed that this allocation allows the driver to perform safe driving while enjoying music.

Based on this, there are two situations where safe driving cannot be performed: when the amount of attention is decreased due to drowsiness; and when an improper attention allocation is made due to distraction. FIG. 9(c) shows an amount of attention in the case of strong drowsiness. Since the arousal level is reduced due to drowsiness, such that the total amount of attention itself has decreased, the amount of attention which is necessary for safe driving (50%) is not ensured, and thus attention calling is needed. On the other hand, FIG. 9(d) shows a case where, although the amount of attention is sufficient, a large amount of attention (50%) is spent for answering a telephone call or the like, such that less than sufficient allocation is given to driving. The latter case will be referred to as a state of distraction in the present specification. In this case, since there is no drowsiness, a method of attention calling which is different from that of FIG. 9(c) is needed.

Hereinafter, the details of the processing by the distraction detection apparatus 100 will be described in order, with reference to flowcharts and the like. After a detailed description of the processing, the feasibility of the present embodiment will be demonstrated by results of an experiment which was performed by the inventors using a driving simulator.

Figure 10:
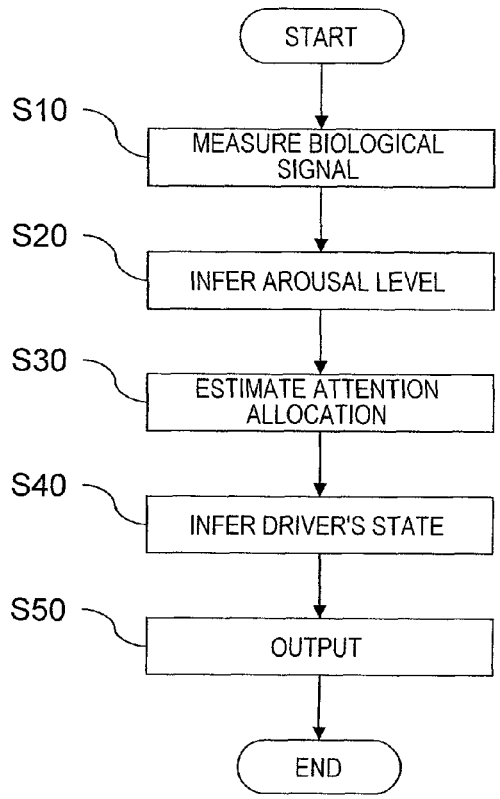
FIG. 10 is a flowchart showing the overall processing by the distraction detection apparatus 100.

FIG. 10 is a flowchart showing the overall processing by the distraction detection apparatus 100.

At step S10, the biological signal detection section 2 acquires an electroencephalogram of the driver. An electroencephalogram is the changes in the potential of the head over time, and is generally measurable with an electroencephalograph which is worn on the head.

At step S20, the arousal level estimation section 3 estimates an arousal level by processing the electroencephalogram signal measured at step S10.

At step S30, the attention allocation estimation section 4 processes the electroencephalogram signal measured at step S10 by a method which is different from that of step S20, and estimates the attention allocation.

At step S40, based on the values of both the arousal level and attention allocation calculated at step S20 and step S30, the driver state estimation section 5 estimates the driver's state. The role of this step is to classify the driver's state into one of the aforementioned three states.

At step S50, based on the driver's state estimated at step S40, the output section 6 performs an intervention with the driver. For example, when state A (sufficient attention is being paid to driving) is determined, no particular output is made because there is no particular problem. When state B (the arousal level is sufficient, but sufficient attention is not being paid to driving) is determined, an output that demands an improved attention allocation to driving is made. When state C (since the arousal level is low, attention to driving is not enough) is determined, an output for improving the arousal level of the driver is made. Examples of outputs will be described later.

Detection of distraction is achieved through the aforementioned flow. Hereinafter, the details of the processes of the respective steps will be described in order.

The biological signal detection section 2 measures an electroencephalogram of the driver. Although an electroencephalograph must be worn by the driver, electroencephalograph devices are becoming downsized and easier to wear, and thus their wearing ease is being improved. The measured electroencephalogram signal of the driver is sent to the arousal level estimation section 3 and the attention allocation estimation section 4 in a wired or wireless manner.

Figure 11:
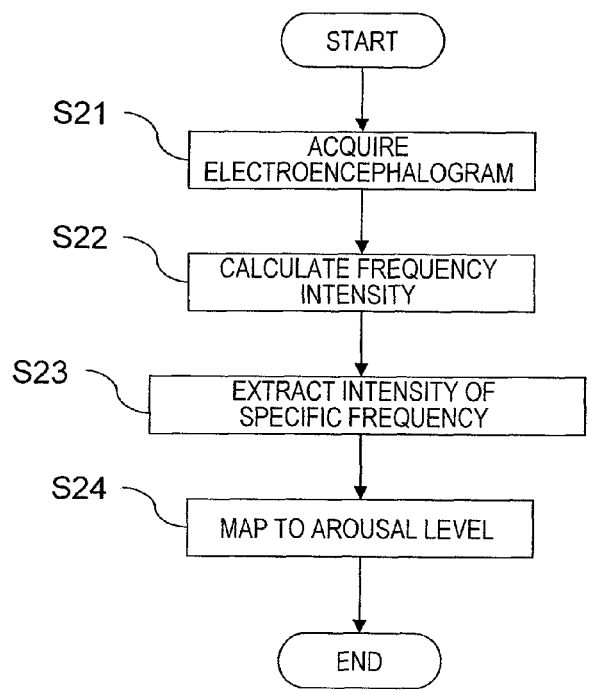
FIG. 11 is a flowchart showing a procedure of processing by an arousal level estimation section 3.

Next, with reference to the flowchart of FIG. 11, the processing by the arousal level estimation section 3 will be described. FIG. 11 is a flowchart showing a procedure of processing by the arousal level estimation section 3.

At step S21, the arousal level estimation section 3 receives the electroencephalogram signal which has been acquired by the biological signal measurement section 2. The range of electroencephalogram to be received differs depending on the situation of the driver and the like. For example, a certain time from a predetermined time before until the present, e.g., 5 minutes of electroencephalogram data from 5 minutes before until the present, is acquired.

At step S22, a signal intensity for each frequency is calculated. An FFT (Fast Fourier Transform) analysis or the like is employed for the calculation.

At step S23, the arousal level estimation section 3 extracts the intensity of a specific frequency. Frequency intensity is supposed to be related to arousal levels. For example, Japanese Laid-Open Patent Publication No. 2007-000280 describes a method of using a ratio between $\alpha$ waves and $\beta$ waves and the like. Since the frequency intensity will be entirely increased when complicated tasks are to be performed, the intensity of the entire frequency band or a specific frequency band may be used, as will be described later.

Note that the arousal level estimation section 3 may determine frequency intensities of the electroencephalogram signal at a plurality of points in time. However, in the case of utilizing the frequency intensities of the electroencephalogram signal at a plurality of points in time, it is preferable that a plurality of groups which are determined based on frequency intensities of the electroencephalogram signal are provided in advance. For example, it is preferable to provide groups of high (H), low (L), and medium (M) frequency intensities that are based on threshold values, in a manner described above. Based on the relationship as to which one is the greater between the frequency intensity of each electroencephalogram signal calculated and the threshold values defining the groups, the arousal level estimation section 3 classifies each frequency intensity into one of the plurality of groups. Then, an average frequency intensity of the group into which the most frequency intensities are classified may be employed as a frequency intensity for use at the next step S24. Alternatively, instead of employing the frequency intensities of the electroencephalogram signal themselves, a frequency intensity which is predefined as an attribute (L, M, H) of each group may be employed as the frequency intensity for use at the next step S24.

At step S24, the arousal level estimation section 3 maps the frequency intensity calculated at step S23 to an arousal level. Arousal levels are psychological quantities, and thus need to be somehow mapped to frequency intensities. The arousal level estimation section 3 retains a rule of mapping between frequency intensities and arousal levels. The mapping rule (method) may be various. For example, the rule may be that the frequency intensity values are assigned straightforwardly to arousal levels, or values of subjective evaluation concerning arousal levels and their corresponding frequency intensities may be previously acquired as data, and a table or mathematical formula defining a relationship therebetween may be retained. Such a table or mathematical formula serves as the mapping rule. Herein, any method may be used that allows an arousal level to be estimated.

Next, with reference to the flowchart of FIG. 12, the processing by the attention allocation estimation section 4 will be described. At the same time, an example of the processing of FIG. 13 will also be described. Note that the waveform in FIG. 13 is only an example for the sake of illustration.

Figure 12:
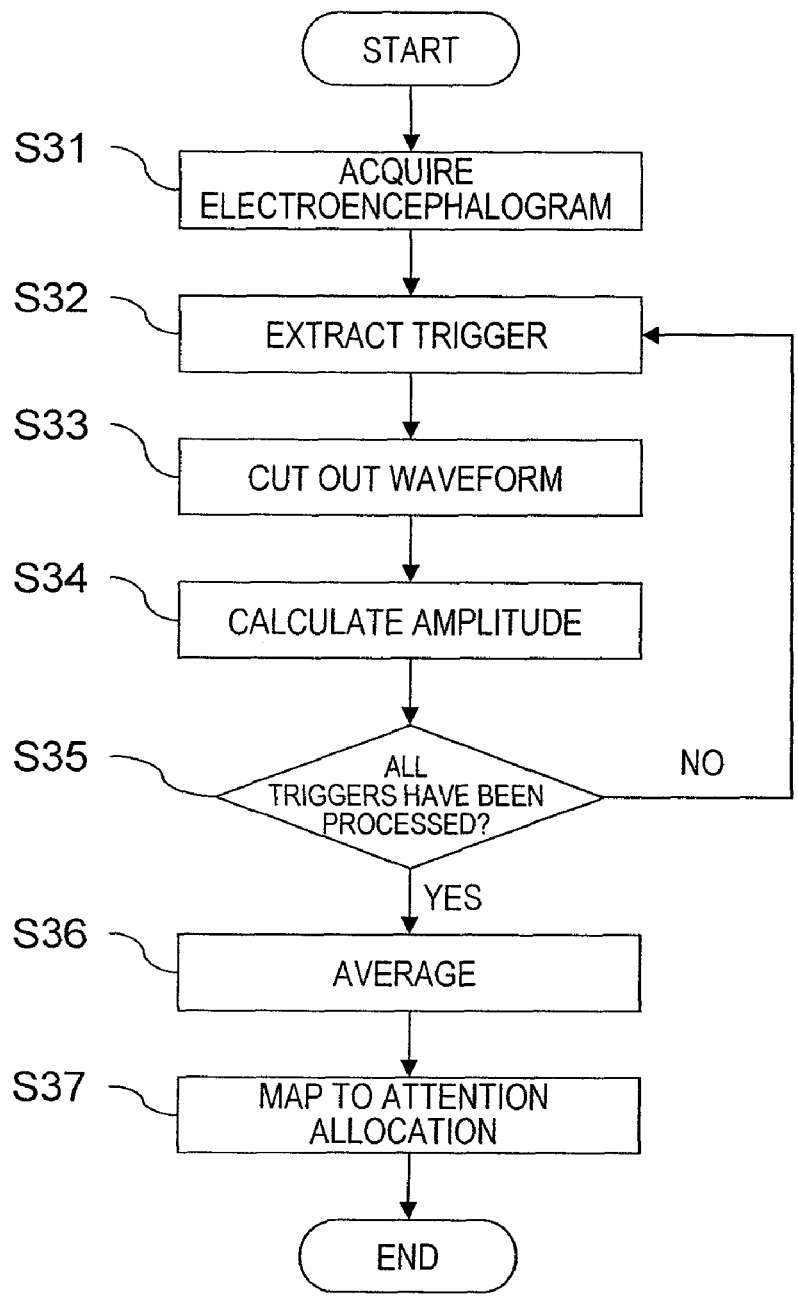
FIG. 12 is a flowchart showing a procedure of processing by an attention allocation estimation section 4.

FIG. 12 is a flowchart describing a procedure of processing by the attention allocation estimation section 4.

Figure 13:
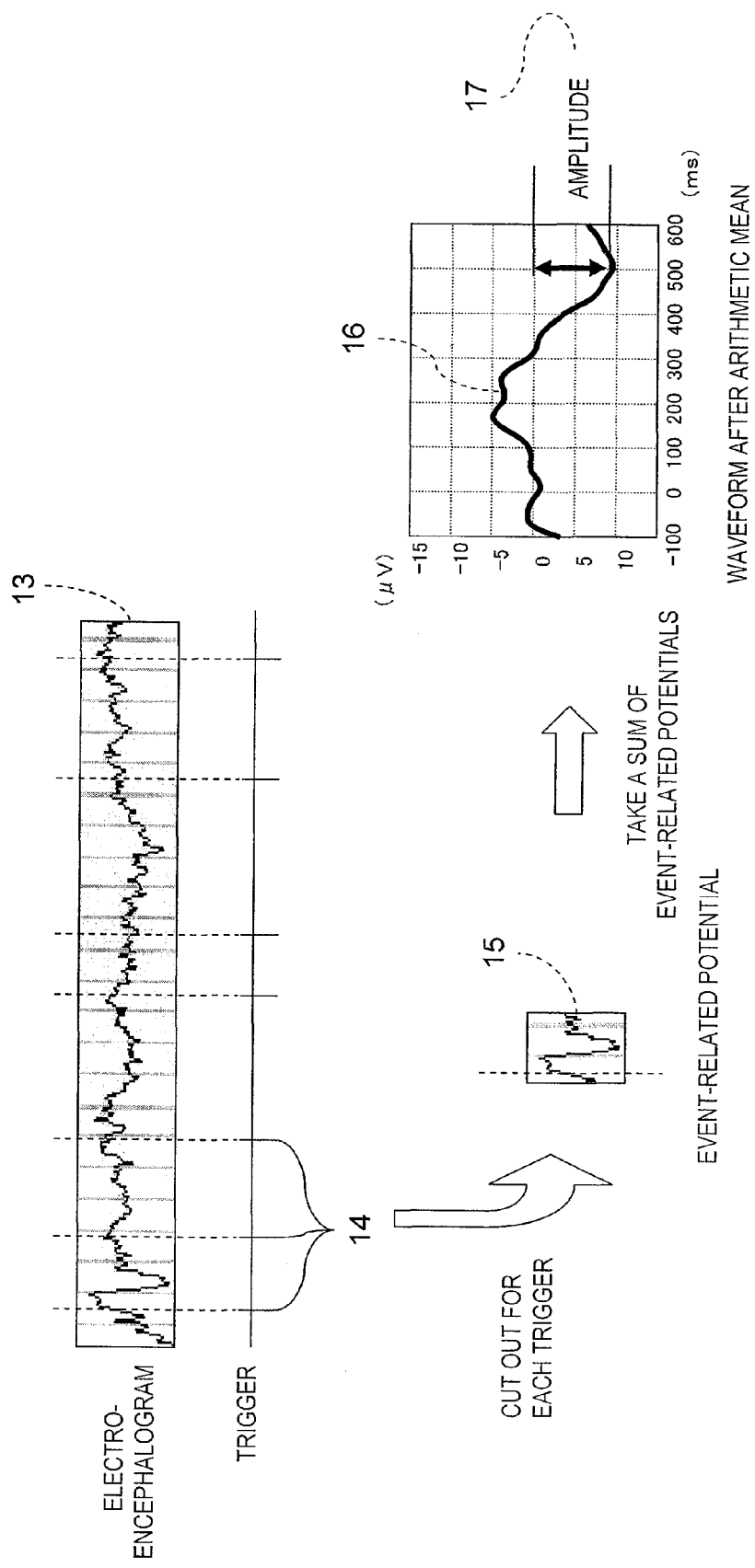
FIG. 13 is a diagram showing processing for obtaining the amplitude of an event-related potential from an electroencephalogram signal.

At step S31 in FIG. 12, the attention allocation estimation section 4 receives the electroencephalogram which is acquired by the biological signal measurement section 2 (electroencephalogram 13 in FIG. 13). The range of the electroencephalogram 13 to be received differs depending on the situation of the driver and the like. For example, a certain time from a predetermined time before until the present point, e.g., 5 minutes of electroencephalogram data from 5 minutes before until the present, is acquired.

It is assumed that triggers 14 also reside in the electroencephalogram data. As used herein, a trigger is the timing of presenting a certain stimulation to the driver, extracted as a signal. The electroencephalogram data before analysis is a record of a sequence of potential changes. By analyzing a zone which is started by a trigger, it becomes possible to analyze an event-related potential of the driver with respect to a stimulation, and the level of attention can be grasped. As stimulations to be presented to the driver other than driving, which may serve as starting points of this attention detection, presentations of an audio or effect sound from the car navigation system, presentations of information on instruments or an information display within the car, and the like may be used. Based on the amplitude of an event-related potential with respect to any such stimulation other than driving, it becomes possible to determine the amount of attention to the simultaneously-performed driving task.

Moreover, the triggers 14 may be recorded in a channel other than the electroencephalograms during electroencephalogram measurement, and may be recorded on another recording means in temporal synchronization.

At step S32, the attention allocation estimation section 4 extracts a trigger 14 from the data acquired at step S31. For the attention allocation estimation, the amplitude of a peak point of the P300 component of an event-related potential or the like is used, for example, and trigger information 14 indicating a starting point for acquiring that event-related potential is necessary. The trigger information 14 contains information as to which event has occurred at which point in time. The electroencephalogram acquired at step S31 contains a plurality of triggers 14 corresponding to a plurality of events.

At step S33, the attention allocation estimation section 4 cut outs a waveform. By using the timing of the trigger information 14 extracted at step S32, electroencephalogram data is cut out as an event-related potential 15 spanning a range from e.g. −200 milliseconds to 600 milliseconds based on that timing. This range to be cut out may be changed depending on the nature of the event-related potential to be used or the like.

At step S34, an amplitude 17 of the electroencephalogram data (event-related potential) which is cut out at step S33 is calculated. In the case of using a P300 signal with respect to an event, a method of using a potential value when the largest positive occurs within a range from 200 to 500 milliseconds may be employed, for example. Supposedly, there exists a relationship between the amount of attention to a given event and the amplitude level, such that the amplitude increases as the amount of attention increases (see, supra, "Measuring attention to video clips: An application of the probe stimulus technique using event-related brain potentials"). This calculated amplitude is once recorded to a memory (not shown) for processing at step S36. As the method of amplitude calculation, it may be calculated after taking an arithmetic mean of the waveforms.

At step S35, the attention allocation estimation section 4 determines whether processing for all triggers has been completed or not. If processing for all triggers has been completed, control proceeds to step S36 (YES); if it has not been completed, control proceeds to step S32 (NO).

If the plurality of amplitude data for the plurality of waveforms have been obtained at step S34, the attention allocation estimation section 4 calculates an average 17 of these values at step S36. Since an electroencephalogram has a large fluctuation in each single trial, by taking an arithmetic mean thereof, it becomes possible to calculate a stabilized waveform 16 and amplitude 17 thereof.

Note that the attention allocation estimation section 4 may calculate a plurality of amplitudes of event-related potentials of the electroencephalogram signal at a plurality of points in time. However, in the case of utilizing amplitudes of event-related potentials at a plurality of points in time, as in the case of the arousal level estimation section 3, it is preferable that a plurality of groups which are determined based on amplitude are provided in advance. For example, it is preferable to provide groups of high (H), low (L), and medium (M) amplitudes that are based on threshold values, in a manner described above. Based on the relationship as to which one is the greater between the amplitude of each event-related potential calculated and the threshold values defining the groups, the attention allocation estimation section 4 classifies each amplitude into one of the plurality of groups. Then, an average amplitude of the group into which the most amplitudes have been classified may be employed as an amplitude for use at the next step S24. Alternatively, instead of employing the amplitudes of the event-related potentials of the electroencephalogram signal themselves, an amplitude which is predefined as an attribute (L, M, H) of each group may be employed as the amplitude for use at the next step S37.

At step S37, the attention allocation estimation section 4 maps the average value of amplitude calculated at step S36 to an amount of allocated attention. The attention allocation estimation section 4 retains a rule of mapping between average values of amplitude and amounts of allocated attention. The mapping rule (method) may be various. For example, average values of amplitude and amounts of allocated attention may be previously acquired as data, and a table or mathematical formula that defines a mapping therebetween may be retained. Such a table or mathematical formula serves as the mapping rule.

Figure 14:
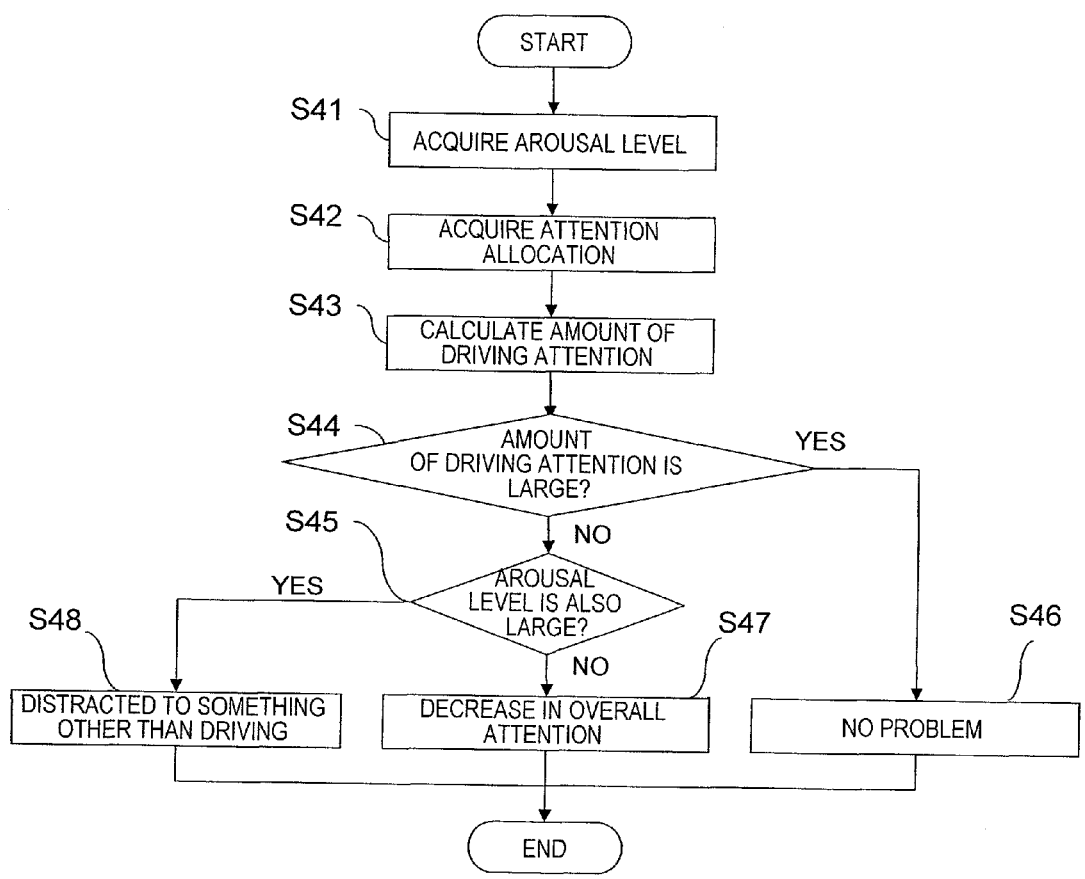
FIG. 14 is a flowchart showing a procedure of processing by a driver state estimation section 5.

Next, with reference to the flowchart of FIG. 14, the processing by the driver state estimation section 5 will be described. At step S41, the driver state estimation section 5 acquires an estimation result of arousal level from the arousal level estimation section 3.

At step S42, the driver state estimation section 5 acquires an estimation result of attention allocation from the attention allocation estimation section 4.

At step S43, the driver state estimation section 5 calculates an amount of driving attention. The amount of driving attention is calculated by the following equation.

$$\text{Amount of driving attention} = \text{arousal level} * (1 - \text{attention allocation})$$

Herein, the "amount of driving attention" takes a value in the range from 0 to 1, and represents ultimately how much attention is being paid to driving. Also, the "attention allocation" takes a value in the range from 0 to 1, and represents, between the attention allocated to driving and the attention allocated to a task other than driving, a proportion of the attention allocated to the task other than driving. Therefore, (1−attention allocation) corresponds to the proportion of the attention that is directed to driving. Thus, the inventors have defined that the amount of driving attention is determined as a product between the arousal level and the proportion of attention that is directed to driving.

Based on the definition according to this equation, it is possible to express a situation where, in spite of a large proportion of attention being directed to driving, the amount of attention to driving is insufficient due to a low arousal level, and a situation where a sufficient arousal level ensures an amount of attention that enables safe driving in spite of a small proportion of attention being directed to driving, and so on.

At step S44, it is determined whether the amount of driving attention has a sufficient value or not. If there is a sufficient amount of driving attention (YES), it is determined at step S46 that there is no particular problem (state A). On the other hand, if it is sufficient (NO), control proceeds to step S45.

At step S45, the driver state estimation section 5 again confirm whether the arousal level is sufficient or not. If the arousal level is high (YES), a state of distraction (state B) is determined at step S48 (where attention is being paid to a task other than driving). If the arousal level is low, a decrease in the overall attention is determined at step S47 (state C).

Through step S46 to step S48, a driver state determination corresponding to each of the above conditions is made, and the result of determination is sent to the output section next.

Next, the operation of the output section 6 will be described. Based on the driver's state determined by the driver state estimation section 5, the output section 6 may make an output from the apparatus 100 to the driver as necessary.

Examples of output methods from the output section 6 to the driver may be various, e.g., calling out to the driver with an audio, presentation of an operating sound or an alarm sound, presentation of text or images on a car navigation system or a head-up display, direct presentation of information using an AR (Augmented Reality) technique, which involves displaying an image or the like on the head-up display in overlay on an object which needs attention, attention calling through a vibration of the steering wheel or the like, and indirect intervention through a smell or adjustment of an amount of fanned air.

The states where intervention from the output section 6 to the driver is necessary are state B and state C described above. However, this is only an example, and the intervention to the driver may be made only in state C.

State B is a state where the arousal level is sufficient, but sufficient attention is not being paid to driving. Therefore, no intervention is necessary for awakening the driver, who already has a sufficient arousal level. As a manner of intervention in state B, a voice guidance for drawing attention to driving such as "Attention to driving is not enough. Concentrate on driving.", or a voice guidance for explaining an exterior situation, e.g., "The road is congested. Concentrate on driving.", may be possible.

State C is a state where the arousal level is so low that there is not enough attention to driving. Therefore, in state C, basically an intervention for increasing the arousal level needs to be made. Specifically, the automobile may suggest taking a break through a loudspeaker, e.g., "You seem very drowsy. Why not take a break?", open a window, or intensify the wind from the air conditioner, for example. Thus, it will be effective to perform a control for increasing the arousal level.

Through such processing, when it is determined that the amount of attention to driving is not enough through classification of the driver's state from an electroencephalogram signal, assistance is provided to improve the driver's state. This makes possible an assistance which better corresponds to the driver's state than conventionally. Moreover, because of the appropriate assistance being provided for the driver, the driver will have an increased trust in the device, which in turn will promote the response of the driver to any output made from the device, thus approaching the goal of providing assistance in safe driving.

As a trigger for an event-related potential corresponding to a task other than driving, a response to specific information on the display is used in the above analysis. Alternatively, the timing of generating an audio or an effect sound, or the timing of presenting text, from the car navigation system or the like may also be utilized. Alternatively, response to an utterance in a conversation with someone in the car or the like may also be utilized.

In Embodiment 1, it is assumed that the arousal level estimation section 2 and the attention allocation estimation section 3 perform processing by using five minutes of electroencephalogram. However, this can be made shorter, depending on improvements in the processing accuracy, and the number of triggers contained in the trial time. In order to make a determination with an electroencephalogram spanning a shorter time, not only utilizing the response to information which is displayed on a single display as in the present experiment, but it would also be effective to aggregate event-related potentials to various responses. This will make for an increase in the triggers occurring per unit time, whereby the electroencephalogram data for analysis can be increased.

Also through developments of anti-noise measures and highly accurate techniques of event-related potential extraction, the required span of electroencephalogram can be reduced. As for processing methods for event-related potentials from a small number of trials, vigorous studies are being made in the field of electroencephalogram interface studies, and by combining these techniques, the required number of event-related potentials can be reduced.

Moreover, the analysis time for an electroencephalogram does not need to be constant. It may be ensured that a constant number of triggers are always contained.

(Embodiment 2)

In Embodiment 1, a state of distraction is determined based only on the driver's state. However, in an actual driving scene, it is expected that the amount of attention which is necessary for safe driving will fluctuate depending on the external environment during driving, e.g., the road situation, weather, time zone, level of congestion, and various other factors. Thus, in order to inform the driver of distraction or the like more accurately, it is necessary to make a determination that takes into consideration a relationship with the external environment.

For example, it is expectable that different amounts of attention are required between traveling on an expressway which has little traffic and offers an unobstructed view and traveling through a crowded shopping mall. It is also expectable that the amount of attention required for driving differs depending on the weather and the road surface situation. By making it possible to adjust the intervention from the driver to the output section 6 in accordance with such situations, a more appropriate intervention for the driver can be realized.

The distraction detection apparatus according to the present embodiment determines a driver's state after performing a comparison with the external environment.

The present embodiment illustrates an embodiment which, even with the same attention allocation for driving, distinguishes between a case where adequate safe driving is being attained and a case where further attention allocation is necessary because adequate safe driving is not being attained, and based on a comparison with that necessary amount of allocated attention, provides an assistance which is more suited to the driving situation.

Figure 15:
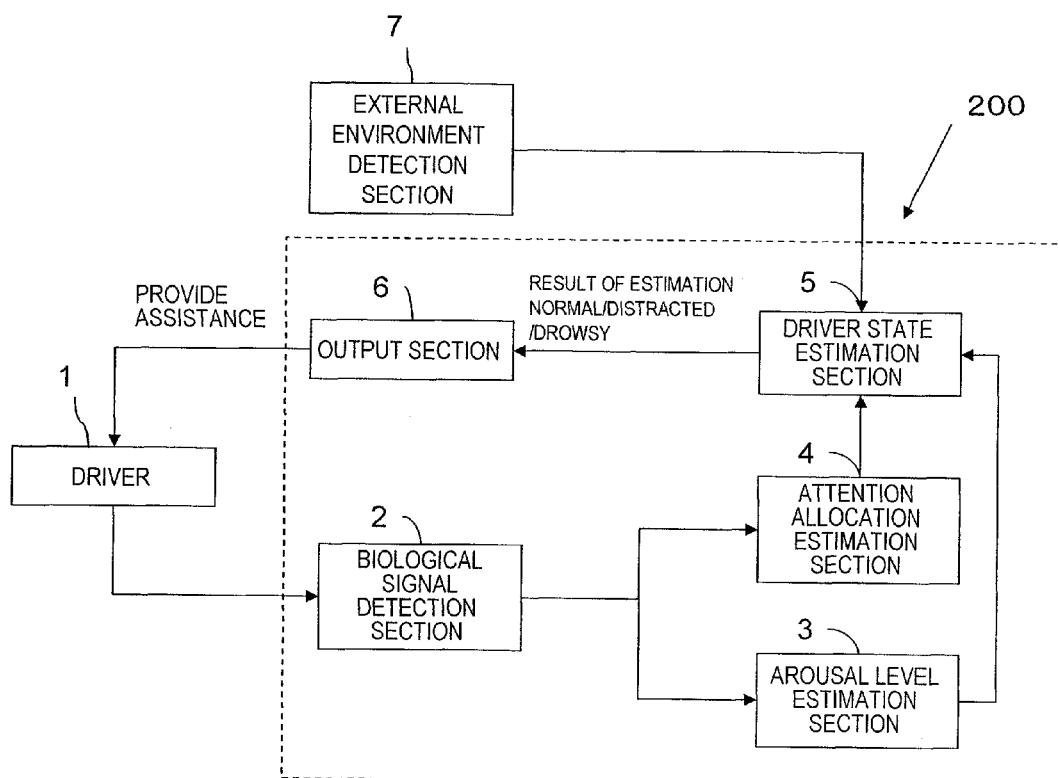
FIG. 15 is a construction diagram showing a distraction detection apparatus 200 according to Embodiment 2.

FIG. 15 is a construction diagram of a distraction detection apparatus 200 according to Embodiment 2 of the present invention. The same reference numerals will be given to constituent elements which are identical to those of Embodiment 1, and the descriptions thereof will be omitted. A difference from Embodiment 1 in terms of constituent elements is that an external environment detection section 7 is provided. The external environment detection section 7 detects a situation outside the car that a driver is faced with. While the difference between Embodiments 1 and 2 that is recognizable from the figure is the absence or presence of the external environment detection section 7, it must also be noted that the processing within the driver state estimation section 5, which receives a signal from the external environment detection section 7, is also different. Therefore, after describing the overall flowchart of Embodiment 2, the detailed processing by the external environment detection section 7 and the driver state estimation section 5 will be described.

Figure 16:
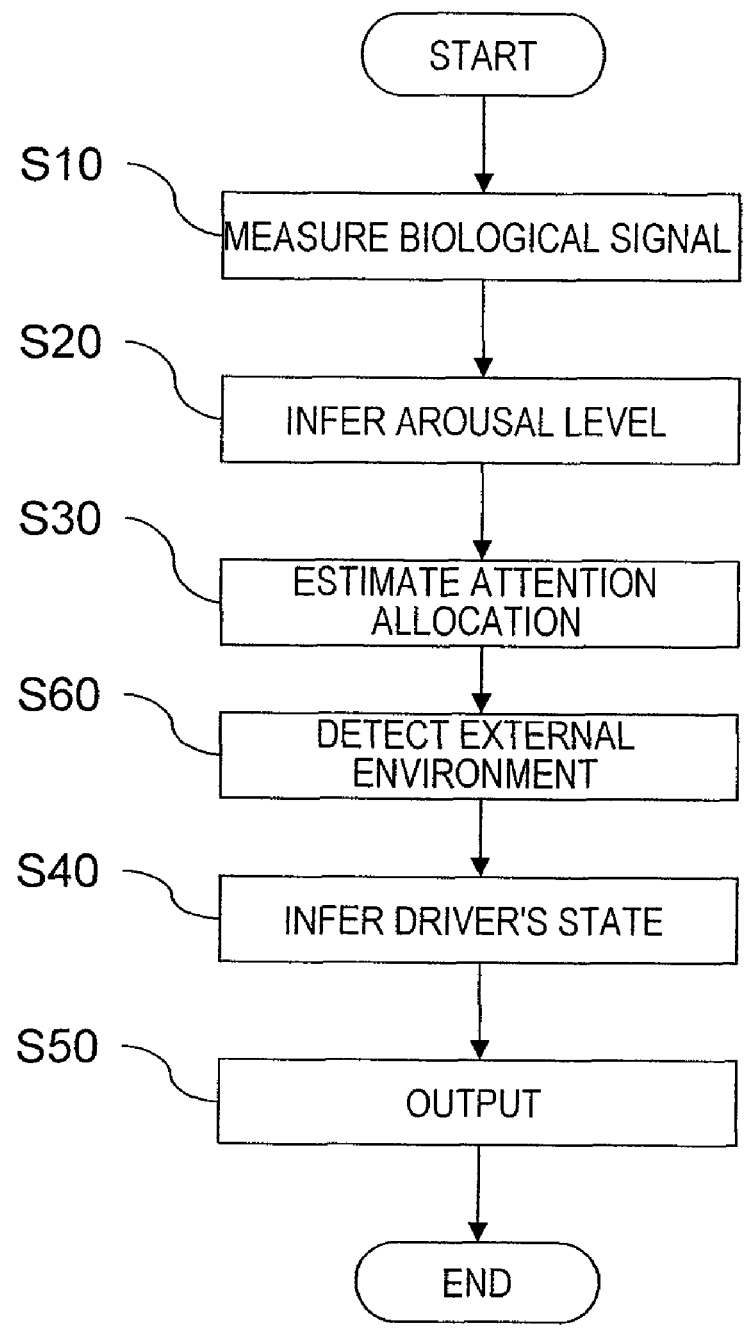
FIG. 16 is a flowchart showing the overall processing by the distraction detection apparatus 200.

FIG. 16 shows a flowchart of the overall processing by the distraction detection apparatus 200. The steps at which the same processes as those in Embodiment 1 are performed will be described only briefly.

At step S10, the biological signal detection section 2 acquires an electroencephalogram of the driver.

At step S20, the electroencephalogram signal measured at step S10 is processed. As a result, an arousal level is estimated by the arousal level estimation section 3.

At step S30, the attention allocation estimation section 4 estimates the attention allocation by utilizing the electroencephalogram signal measured at step S10.

At step S60, the external environment detection section 7 recognizes a situation outside the car. Examples of situations outside the car will be described later.

At step S40, based on both values of arousal level and the attention allocation calculated at step S20 and step S30, the driver state estimation section 5 calculates an amount of attention concerning the driving of the driver. Then, through a comparison with an amount of attention necessary for safe driving which is calculated from the situation outside the car as determined at step S60, the driver's state is classified.

As used herein, the driver's state is one of the three states of a driver as described in Embodiment 1, i.e., the three following states concerning attention:
state A: sufficient attention is being paid to driving;
state B: the arousal level is sufficient, but sufficient attention is not being paid to driving; and
state C: since the arousal level is low, attention to driving is not enough.

The role of step 40 is to classify the driver's state into one of aforementioned three states.

At step S50, based on the driver's state estimated at step S40, the output section 6 performs an intervention with the driver. For example, when state A is determined, no particular output is made because there is no particular problem. However, in state B, an output is made to improve the attention allocation for driving; and in state C, an output is made to improve the arousal level of the driver. Examples of outputs are as described in Embodiment 1.

Next, by using an example of FIG. 17, examples of external environments to be detected by the external environment detection section 7 will be described.

FIG. 17 shows a table storing some factor governing the external situation, and required amounts of attention corresponding thereto. This table may be stored in the driver state estimation section 5, for example.

As factors governing the external situation, the illuminance, which relates to time zones having a high correlation with daily activities such as commutation or shopping and to the ease with which the driver can recognize the external environment (column 40), the road surface situation, which governs the behavior of the car in response to driving operations (column 41), the weather, which relates to the ease of visually recognition of the exterior and the ease of being visually recognized by an oncoming car (column 42), the number of objects to pay attention to (column 43), and the like are listed. Some of these factors may occur in situation in each combination, and the required amount of attention will fluctuate depending on the combination.

In a table format such as FIG. 17, these data may be obtained by previously calculating what amounts of attention are necessary in some situations as a database (as in the column 44), or calculated from the parameters of each situation. That is, it suffices if there are some rules for deriving the required amount of attention from the exterior (i.e., outside the car) environment. For example, ambient illuminance or the like relate to ease of recognition, and the number of objects to pay attention to and the like directly relate to the amount of attention, and therefore they may be allowed to be reflected in the required amount of attention by being multiplied by certain coefficients.

Figure 18:
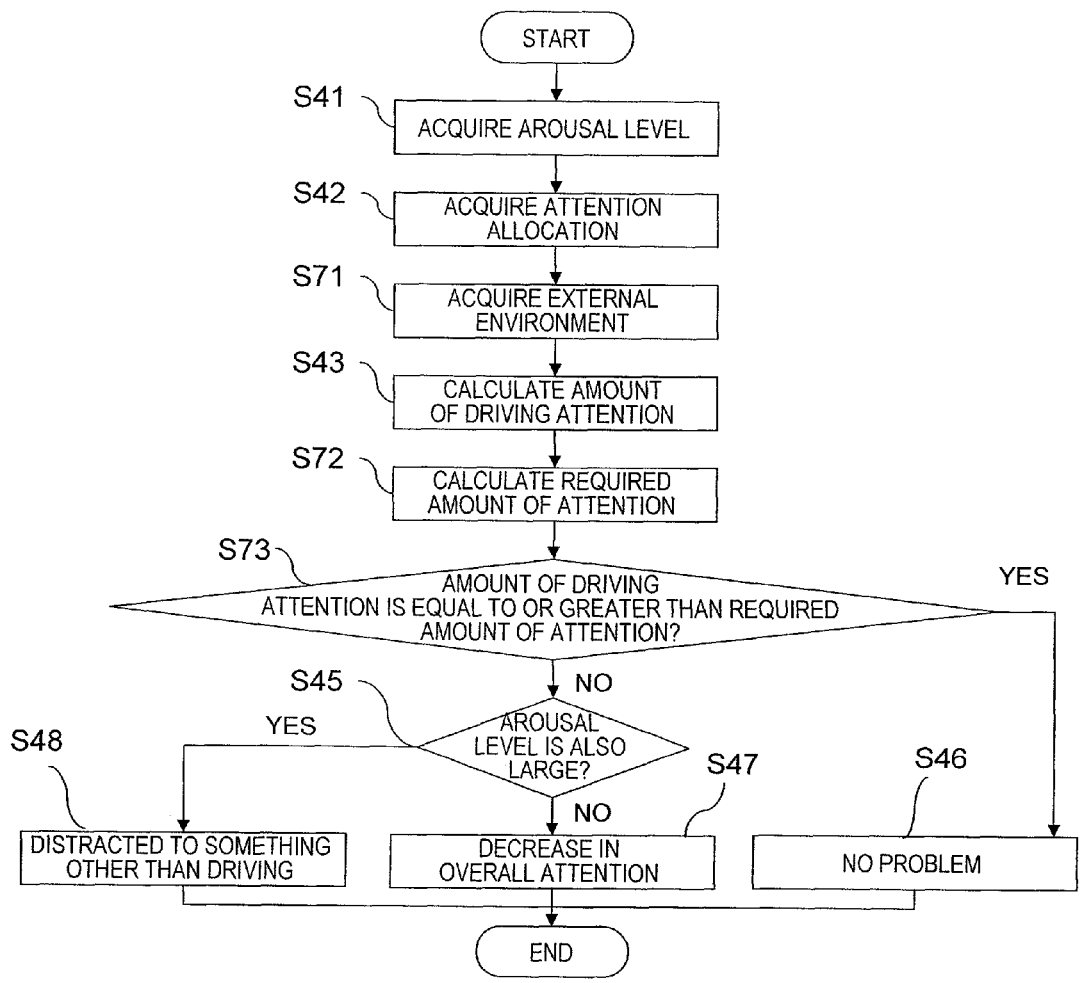
FIG. 18 is a flowchart of a driver state estimation in Embodiment 2.

FIG. 18 shows a flowchart of driver state estimation according to Embodiment 2. The steps at which the same processes as those in Embodiment 1 are performed will be described only briefly.

At step S41, the driver state estimation section 5 acquires an estimation result of arousal level from the arousal level estimation section 3.

At step S42, the driver state estimation section 5 acquires an estimation result of attention allocation from the attention allocation estimation section 4.

At step S71, the driver state estimation section 5 acquires a situation of the external environment from the external environment detection section 7.

At step S43, the driver state estimation section 5 calculates an amount of driving attention. The amount of driving attention is calculated according to the following equation: amount of driving attention=arousal level*(1−attention allocation).

At step S72, the driver state estimation section 5 calculates a required amount of attention. This may be done by referring to a corresponding required amount of attention in a table format as illustrated in FIG. 17, or determined from previously determined rules or the like.

At step S73, the driver state estimation section 5 compares the current amount of driving attention of the driver as calculated at step S43 against the required amount of attention calculated at step S72. If the amount of driving attention is greater than the required amount of attention (YES), a classification is made at step S46 that sufficient attention is being paid to driving. If it is determined that the amount of driving attention is smaller than the required amount of attention (NO), control proceeds to step S45.

At step S45, the driver state estimation section 5 again confirms whether the arousal level is sufficient or not. If the arousal level is high (YES), a classification is made at step S48 to establish a state of distraction where attention is being paid to a task other than driving. If the arousal level is low, a classification is made at step S47 that the overall attention is low.

Through step S46 to step S48, the driver state estimation section 5 makes a driver state determination corresponding to each of the above conditions, and the information of the result of determination is sent to the output section next.

Through such driver state determination, it is possible to classify a driver's state which is suitable to the road situation, rather than making a determination based on a fixed amount of attention which is previously set, such that attention calling is performed for the driver only when necessary. As a result, situations of excess or lack of alarms can be reduced.

As a starting point of an event-related potential concerning a task other than driving in the embodiments, the timing of presenting a message on a car navigation system or the like in the car (which corresponds to a display-viewing task) can be utilized, as carried out by the inventors. As other visual stimulations, visual stimulation presenting devices for event-related potential measurement may be provided in the car. For example, LEDs may be installed on both sideview mirrors, a car navigation system, the speedometer section, or the like, and the timing of flickering such visual stimulation presenting devices may be utilized.

As an auditory stimulation, in a combined output from a car navigation system in which a sound for calling attention is followed by a message, e.g., "(pong) Turn right next", the timing of generating the sound for calling attention may be utilized. Alternatively, the timing of a sudden change in the sound while listening to the radio or music may be utilized.

Moreover, other than visual or audio stimulations, a stimulation to the somatic sensation will also be effective. For example, the steering wheel or the seat of the driver may occasionally vibrate, and an event-related potential with respect to that vibration may be measured so as to be utilized as information that reflects attention to tasks other than driving.

It is desirable that events outside the car, as contrasted to car driving, are clear stimulations. Examples of clear stimulations include timing at which a traffic light changes. A traffic light turning red, which requires a braking operation or preparation for braking to be made, is a timing at which changes in attention are easily caught. Similarly, as an auditory stimulation, an alarm sound from an ambulance can be used; or as a somatic stimulation, a vibration of the tires stepping on a white line can be used.

The processing by the distraction detection apparatus concerning each of the Embodiments described above can be implemented as a program to be executed by a computer. For example, any processing that has been described by using a flowchart can be realized as a computer program defining that procedure of processing. Such a computer program may be distributed on the market as a product recorded on a storage medium, such as a CD-ROM, or transmitted via telecommunication lines such as the Internet.

All or some of the constituent elements composing the above-described distraction detection apparatus may be implemented as a general-purpose processor (semiconductor circuit) executing a computer program. Alternatively, they may be implemented as a special processor in which such a computer program and a processor are integrated. For example, a general-purpose processor may be provided in the distraction detection apparatus of Embodiment 1, and as this processor executes a computer program, it may function as all or some of the arousal level estimation section 3, the attention allocation estimation section 4, and the driver state estimation section 5.

Note that the illustrated distraction detection apparatus does not need to be accommodated within a single housing. For example, when an electroencephalograph is employed as the biological signal detection section, the electroencephalograph may be connected in a wired or wireless manner to the other constituent elements of the distraction detection apparatus. Moreover, a computer which is provided in a remote place via a communications network may function as all or some of the arousal level estimation section 3, the attention allocation estimation section 4, and the driver state estimation section 5.

The estimation of a driver's state by the distraction detection apparatus according to the present invention is applicable to a wide variety of industries. For example, it is applicable to any industry where attention to driving, operation, and the like is necessary, concerning not only drivers of common vehicles, but also drivers of vehicles for business uses (e.g., drivers of trucks, taxis, or buses), operators of vehicles other than cars (trains, airplanes, and marine vessels), plant supervisors (e.g., those in factories), and so on.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A distraction detection apparatus comprising:
   an electroencephalogram detection section for detecting an electroencephalogram signal of a driver;
   an arousal level estimation section for retaining a first rule of mapping parameter values of an electroencephalogram signal to arousal levels, and estimating an arousal level based on the detected electroencephalogram signal and the first rule;
   an attention allocation estimation section for retaining a second rule of mapping parameter values of an electroencephalogram signal to attention allocations, and estimating an attention allocation based on the detected electroencephalogram signal and the second rule;
   a driver state estimation section for retaining a third rule of deriving an amount of attention from an arousal level and an attention allocation, estimating an amount of attention of the driver paid to driving based on the estimated arousal level and attention allocation and the third rule, and classifying a state of the driver into a normal state, a state of reduced attention, or a state of reduced arousal level; and
   an output section for performing an intervention for the driver based on a result of classification by the driver state classification section.

2. The distraction detection apparatus of claim 1, wherein, the first rule maps frequency intensities of an electroencephalogram signal to arousal levels; and the arousal level estimation section calculates a frequency intensity of the detected electroencephalogram signal, and estimates the arousal level based on a result of calculation and the first rule.

3. The distraction detection apparatus of claim 2, wherein, a plurality of groups are previously defined in the arousal level estimation section, each group being defined based on a frequency intensity of an electroencephalogram signal; and
the arousal level estimation section classifies frequency intensities of the detected electroencephalogram signal as calculated at a plurality of points in time, each frequency intensity being classified into one of the plurality of groups, and estimates the arousal level based on at least one frequency intensity that is classified into one of the plurality of groups and on the first rule.

4. The distraction detection apparatus of claim 1, wherein, the second rule maps amplitudes of event-related potentials of an electroencephalogram signal to attention allocations; and
the attention allocation estimation section calculates an amplitude of an event-related potential of the detected electroencephalogram signal, and estimates the attention allocation based on a result of calculation and the second rule.

5. The distraction detection apparatus of claim 4, wherein, a plurality of groups are previously defined in the attention allocation estimation section, each group being defined based on an amplitude of an event-related potential; and
the attention allocation estimation section classifies amplitudes of the event-related potential of the detected electroencephalogram signal as calculated at a plurality of points in time, each amplitude of the event-related potential being classified into one of the plurality of groups, and estimates the attention allocation based on at least one amplitude of the event-related potential that is classified into one of the plurality of groups and on the second rule.

6. The distraction detection apparatus of claim 1 further comprising an external environment detection section for detecting an external environment, wherein
the driver state estimation section has a rule of deriving a required amount of attention based on a detected external environment, and compares the amount of attention paid to driving as estimated by the driver state estimation section against a required amount of attention derived by applying the rule to the external environment detected by the external environment detection section, thus determining whether the driver is paying attention to complexity in the external environment.

7. The distraction detection apparatus of claim 1, wherein the driver state estimation section calculates an amount of attention of the driver paid to driving by multiplying the arousal level estimated by the arousal level estimation section and an attention allocation to driving estimated by the attention allocation estimation section.

8. The distraction detection apparatus of claim 1, wherein, the attention allocation estimation section has a rule defining a relationship between an attention allocation to a task other than driving and an attention allocation to driving, and is capable of estimating an attention allocation to driving based on an attention allocation to the task other than driving and the rule; and
the driver state estimation section calculates an amount of attention of the driver paid to driving by multiplying the arousal level estimated by the arousal level estimation section and the attention allocation to driving estimated by the attention allocation estimation section.

9. A distraction detection method, comprising the steps of:
providing a first rule of mapping parameter values of an electroencephalogram signal to arousal levels;
providing a second rule of mapping parameter values of an electroencephalogram signal to attention allocations;
providing a third rule of deriving an amount of attention from an arousal level and an attention allocation;
detecting an electroencephalogram signal of a driver using an electroencephalogram detection section;
estimating an arousal level based on the detected electroencephalogram signal and the first rule using an arousal level estimation section;
estimating an attention allocation based on the detected electroencephalogram signal and the second rule using an attention allocation estimation section;
estimating an amount of attention of the driver paid to driving based on the estimated arousal level and attention allocation and the third rule, and classifying a state of the driver into a normal state, a state of reduced attention, or a state of reduced arousal level using a driver state estimation section; and
performing an intervention for the driver based on a result of classification by the classifying step using an output section.

10. A non-transitory computer-readable medium storing a computer program thereon which, when, executed by a computer, causes the computer to execute the steps of:
receiving an electroencephalogram signal of a driver;
estimating an arousal level based on the detected electroencephalogram signal of the driver and a first rule of mapping parameter values of an electroencephalogram signal to arousal levels;
estimating an attention allocation based on the detected electroencephalogram signal and a second rule of mapping parameter values of an electroencephalogram signal to attention allocations;
estimating an amount of attention of the driver paid to driving based on the estimated arousal level and attention allocation and a third rule of deriving an amount of attention from an arousal level and an attention allocation, and classifying a state of the driver into a normal state, a state of reduced attention, or a state of reduced arousal level; and
performing an intervention for the driver based on a result of classification by the classifying step.

* * * * *